(12) United States Patent
Allen

(10) Patent No.: US 11,013,874 B2
(45) Date of Patent: May 25, 2021

(54) METHODS AND SYSTEMS FOR OBTAINING DESIRED OXYGEN CONCENTRATIONS AND AIR FLOWS DURING RESPIRATORY THERAPY

(71) Applicant: Vapotherm, Inc., Exeter, NH (US)

(72) Inventor: John Allen, North Andover, MA (US)

(73) Assignee: Vapotherm, Inc., Exeter, NH (US)

( * ) Notice: Subject to any disclaimer, the term of this patent is extended or adjusted under 35 U.S.C. 154(b) by 1075 days.

(21) Appl. No.: 14/983,212

(22) Filed: Dec. 29, 2015

(65) Prior Publication Data
US 2017/0182278 A1 Jun. 29, 2017

(51) Int. Cl.
*A61M 16/00* (2006.01)
*A61M 16/12* (2006.01)
*A61M 16/10* (2006.01)

(52) U.S. Cl.
CPC ...... *A61M 16/0051* (2013.01); *A61M 16/108* (2014.02); *A61M 16/12* (2013.01); *A61M 2016/0039* (2013.01); *A61M 2016/1025* (2013.01); *A61M 2202/0208* (2013.01); *A61M 2205/3368* (2013.01); *A61M 2205/505* (2013.01); *A61M 2205/581* (2013.01); *A61M 2205/583* (2013.01); *A61M 2205/8206* (2013.01)

(58) Field of Classification Search
CPC ............ A61M 16/0051; A61M 16/108; A61M 16/12; A61M 16/0039; A61M 16/021; A61M 16/022; A61M 16/024
See application file for complete search history.

(56) References Cited

U.S. PATENT DOCUMENTS

| | | | |
|---|---|---|---|
| 6,041,777 A | 3/2000 | Faithfull et al. | |
| 7,886,740 B2 | 2/2011 | Thomas et al. | |
| 7,993,279 B2 | 8/2011 | Hartley et al. | |
| 9,233,218 B2 | 1/2016 | Chapman et al. | |
| 9,555,209 B2 | 1/2017 | Klein | |
| 2003/0145855 A1* | 8/2003 | Fuhrman ........... | A61M 16/0096 128/204.18 |
| 2008/0078389 A1* | 4/2008 | Xiao ..................... | A61M 16/12 128/204.22 |
| 2010/0175695 A1* | 7/2010 | Jamison ................ | A61M 16/01 128/203.14 |
| 2010/0229867 A1 | 9/2010 | Bertinetti et al. | |
| 2010/0252037 A1 | 10/2010 | Wondka et al. | |
| 2012/0272957 A1* | 11/2012 | Chapman .......... | A61M 16/0045 128/203.12 |
| 2015/0020801 A1* | 1/2015 | Frame ............... | A61M 16/1005 128/202.22 |
| 2016/0193438 A1* | 7/2016 | White ............... | A61M 16/0096 128/203.12 |
| 2016/0287824 A1* | 10/2016 | Chang ............... | A61M 16/0066 |

\* cited by examiner

*Primary Examiner* — Margaret M Luarca
(74) *Attorney, Agent, or Firm* — White & Case LLP

(57) ABSTRACT

Methods, systems, and apparatuses are described that indicate an amount at which various gas flow rates should be manually adjusted in order to achieve targeted total flow rates and concentration levels.

23 Claims, 11 Drawing Sheets

```
1.   #include "FlowAssistant.h"                                          900
2.   #include "Interfaces.h"
3.   #include "FlowSensor.h"
4.   #include "OxygenSensor.h"
5.   FlowAssistant::FlowAssistant(FlowSensor* flowSensor, OxygenSensor* o2Sensor)
6.     : _flowSensor(flowSensor),
7.       _o2Sensor(o2Sensor),
8.       TargetO2Pcnt(21.0, "TargetO2Pcnt"),
9.       TargetTotalFlow(10.0, "TargetTotalFlow"),
10.      TargetAirFlow(0.0, "TargetAirFlow"),
11.      TargetO2Flow(0.0, "TargetO2Flow"),
12.      ErrorAirPcnt(50.0, "ErrorAirPcnt"),
13.      ErrorO2Pcnt(50.0, "ErrorO2Pcnt")
14.  {
15.      connect(&_flowSensor->FlowRate, SIGNAL(Changed()), this, SLOT(UpdateFlows()));
16.      connect(&_o2Sensor->Oxygen, SIGNAL(Changed()), this, SLOT(UpdateFlows()));
17.      UpdateFlows();
18.  }
19.  void FlowAssistant::SetTargetO2Pcnt(double pcnt)
20.  {
21.      if (pcnt < 21.0) pcnt = 21.0;
22.      if (pcnt > 100.0) pcnt = 100.0;
23.      TargetO2Pcnt = pcnt;
24.      UpdateFlows();
25.  }
26.  void FlowAssistant::SetTargetTotalFlow(double flow)
27.  {
28.      if (flow < 1.0) flow = 1.0;
29.      if (flow > 40.0) flow = 40.0;
30.      TargetTotalFlow = flow;
31.      UpdateFlows();
32.  }
33.  void FlowAssistant::UpdateFlows()
34.  {
35.      TargetAirFlow = TargetTotalFlow.Get() * (1 - TargetO2Pcnt.Get() / 100.0) / 0.79;
36.      TargetO2Flow = TargetTotalFlow.Get() - TargetAirFlow.Get();
37.      double totalFlow = _flowSensor->FlowRate.Get();
38.      double o2Pcnt = _o2Sensor->Oxygen.Get();
39.      double airFlow = totalFlow * (1 - o2Pcnt / 100.0) / 0.79;
40.      double o2Flow = totalFlow - airFlow;
41.      ErrorAirPcnt = 2*(airFlow - TargetAirFlow.Get()) + 50;
42.      ErrorO2Pcnt = 2*(o2Flow - TargetO2Flow.Get()) + 50;
43.  }
```

FIG. 9

METHODS AND SYSTEMS FOR OBTAINING DESIRED OXYGEN CONCENTRATIONS AND AIR FLOWS DURING RESPIRATORY THERAPY

BACKGROUND

Patients with respiratory ailments may be treated with respiratory assist devices, for example devices that deliver supplemental breathing gas to a patient. Ideally gas lowers respiration rate, improves secretion clearance, and reduces the work of breathing, which allows patients to comfortably eat, speak, and sleep, while receiving a high level of respiratory support.

Unfortunately, many patients may desire to receive this type of treatment in the comfort of their home or in non-clinical settings. In such settings, access to the high pressure gas needed for many respiratory assist devices to function may not be readily available. For example, many devices that automatically blend gas (e.g., oxygen) to a desired concentration require a gas source capable of producing pressure at at least fifty psi. In many cases, this amount of pressure is only available via specialized gas sources, which may dampen accessibility, reduce the portability, and completely preclude the use of auto-blending devices in many hospital units, step-down units, long-term care units, the home, and any place without an access to a source of high pressure gas.

SUMMARY

Accordingly, methods, systems, and apparatuses are described herein that allow patients at locations without sources of high pressure gas to receive the benefits of respiratory assist therapy. Specifically, the device described herein is configured to provide respiratory assist therapy without requiring a gas source capable of producing pressure at at least fifty psi.

For example, as described below, the device generates for display indications for how to adjust lower pressure gas sources during respiratory assist therapy to achieve the same benefits as their high pressure gas source counterparts. Moreover, the device described herein does so without the need for the expensive components needed to auto-blend gas as found in these high pressure gas source counterparts.

Additionally, anticipating the use of the device in non-clinical settings, the device provides intuitive indications that are designed to provide therapists and patients guidance on using the device without requiring i) a tedious and time-consuming iterative approach to obtaining a specific gas flow and a specific gas concentration or ii) an advanced knowledge of specific gas flows for obtaining specific concentrations.

For example, to achieve the benefits of respiratory assist therapy, patients must receive a flow of gas (e.g., breathable air) with a specific concentration of a key gas (e.g., oxygen). Short of using the auto-blending devices discussed above, therapists and patients rely on manual adjustments of air and oxygen sources. However, to make the correct adjustments, therapists and patients must rely on advanced training and specialized knowledge related to gas flows and resulting concentrations. To alleviate the need for such advanced training and specialized knowledge, the device provides indications of key information that allows for easy operation and delivery of gas flows with specific concentrations.

In some aspects, the device performs a method of assisting a patient during respiratory therapy that may include receiving a user input of a targeted oxygen concentration and a user input of a targeted total air flow. For example, the device allows a therapist or patient to input a specific oxygen concentration and a specific total air flow (e.g., tailored to levels to allow the patient to comfortably eat, speak, and sleep, while receiving the respiratory therapy).

The device may then determine a targeted oxygen flow rate based on the targeted oxygen concentration and the targeted total air flow. For example, using a ratio of an oxygen percentage of the targeted oxygen concentration to an oxygen percentage in the air from the air source, the device automatically selects the targeted air flow rate.

The device may then determine a targeted air flow rate based on the targeted oxygen flow rate and targeted total air flow. For example, as opposed to their high pressure gas source counterparts, the device operates with the use of separate low pressure sources (e.g., sources capable of producing less than fifty psi) of air and oxygen. Therefore, to meet the targeted oxygen flow rate and targeted total air flow, the device must select a specific flow rate of the both air source and the oxygen source. Moreover, as total air flow and oxygen concentration depend on both the flow rate of air and oxygen sources, the selection of these flow rates must be done in concert.

The device may then determine a first oxygen flow rate of oxygen from an oxygen source and a first air flow rate of air from an air source. For example, to determine the progress of the patient to the targeted air flow rate and the targeted oxygen flow rate, the device determines an initial oxygen flow rate and air flow rate.

The device may then determine the differences between the targeted oxygen flow rate and first oxygen flow rate and the targeted air flow rate and the first air flow rate. For example, the device may determine a first difference, which indicates a difference between the targeted oxygen flow rate and the first oxygen flow rate, and a second difference, which indicates a difference between the targeted air flow rate and the first air flow rate.

Finally, the device may generate for display, on a display screen, a first indication that indicates a first amount to manually adjust the first oxygen flow rate to reach the targeted oxygen concentration based on the first difference, and a second amount to manually adjust the first air flow rate to reach the targeted total air flow based on the second difference. For example, in response to determining that the oxygen flow rate must be increased or decreased to reach the targeted oxygen flow rate (associated with both the targeted oxygen concentration and the targeted total air flow) and that the air flow rate must be increased or decreased to reach the targeted oxygen flow rate (associated with both the targeted oxygen concentration and the targeted total air flow), the device may recommend adjustments to the current air flow rate and oxygen flow rate.

In some embodiments, the device may receive a first manual adjustment, in which the first manual adjustment modifies the first oxygen flow rate to a second oxygen flow rate. Accordingly, the device may determine a third difference that indicates a difference between the targeted oxygen flow rate and the second oxygen flow rate and generate for display, on the display screen, a second indication that indicates a second amount to manually adjust the second oxygen flow rate based on the third difference. For example, as the therapist or patient manually adjusts the oxygen flow rate in response to the first indication, the device may continuously update the degree to which further adjustment is needed. By providing this real-time feedback, the therapist or patient may quickly and easily reach the desired oxygen flow rate.

Furthermore, the device may receive a second manual adjustment that modifies the first air flow rate to a second air flow rate. Accordingly, the device may determine a fourth difference that indicates a difference between the targeted air flow rate and the second total air flow rate and the second indication may further indicate a second amount to manually adjust the second air flow rate based on the fourth difference. For example, the oxygen and air flow rates must be done in concert in order to achieve the desired total air flow and oxygen concentration, the device may continuously update the indications of the manual adjustments to each flow rate as needed. Consequently, a therapist or patient may modify both flow rates simultaneously or, simply adjust one flow rate and then the other.

In some embodiments, the device may provide additional feedback to the user. For example, the device may indicate the temperature, humidity, etc. of the gases delivered to the patient (e.g., in order to maximize comfort). Likewise, the device may allow the therapist or patient to set up various alerts. For example, the device may be configured sound and/or display an alert is a particular flow rate, concentration, etc. is below a safety or comfort threshold.

The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

FIG. 9 shows an illustrative example of pseudocode for obtaining desired oxygen concentrations and air flows in accordance with some embodiments of the disclosure;

DETAILED DESCRIPTION OF THE DRAWINGS

Methods, systems, and apparatuses are described herein that indicate an amount at which various gas flow rates should be manually adjusted in order to achieve a targeted total flow rate and oxygen concentration level. For example, in order to meet specific total flow rate and concentration level goals, a device may indicate whether or not a gas flow rate should be adjusted. Moreover, the device may indicate a particular amount that the gas flow rate should be adjusted and continually update that amount as adjustments are made.

Figure 1:
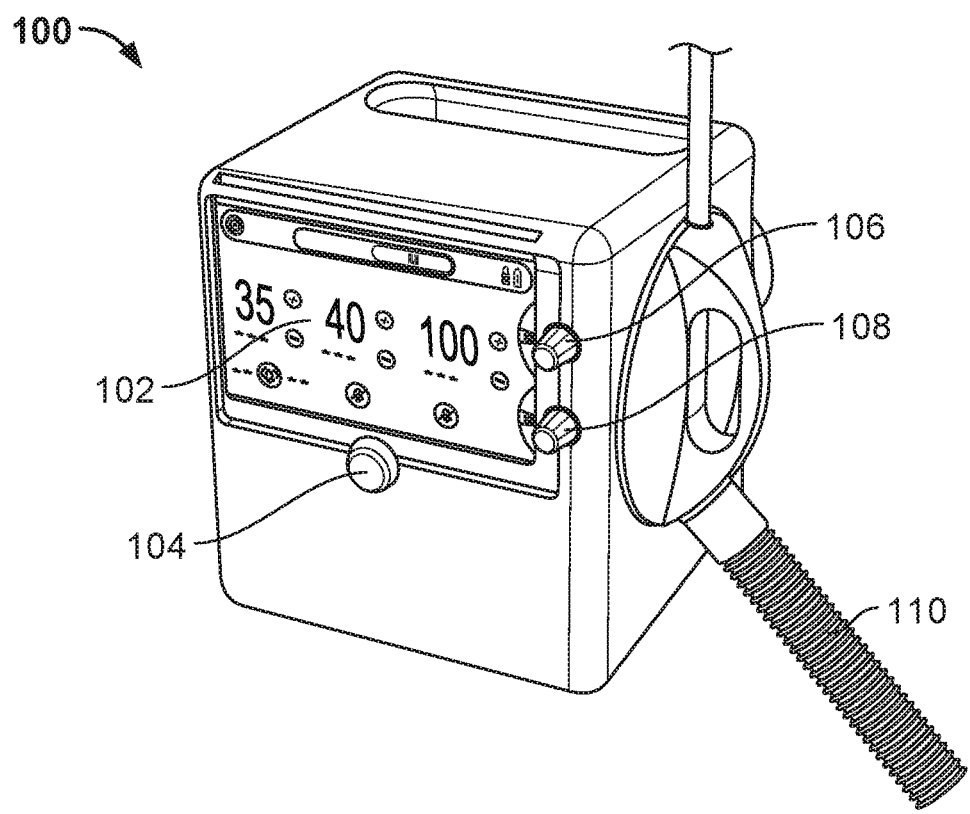
FIG. 1 shows an illustrative example of a device for obtaining desired oxygen concentrations and air flows in accordance with some embodiments of the disclosure.

As referred to herein, the term "device" should be understood to mean any equipment that may be configured to perform the features described herein. One example of a device is shown in FIG. 1. FIG. 1 shows device 100, which is configured to provide feedback to a user related to current air flow rates and oxygen concentration levels. For example, FIG. 1 includes user interface 102. User interface 102 primarily functions to receive user inputs and provide feedback to the user regarding current and desired air flows and current and desired gas concentration levels via one or more indications, as described in more depth below.

Device 100 also includes input 104. Input 104 may allow device 100 to receive various user inputs related to target air flows, concentration level, etc. as well as navigate among the information generated for display in user interface 102. The various functions of user interface 102 and the information provided by it is more fully discussed in relation to FIGS. 4-7 below.

Device 100 also includes output 110. As shown in FIG. 1, output 110 may function as a hose or tube used to deliver gas (e.g., breathable air with a specified concentration of oxygen) to a user. The gas delivered via output 110 may be the subject of various indications shown on user input interface 102. For example, indications describing the progress of a user towards a particular targeted total air flow or targeted oxygen concentration level may correspond to the current air flow and/or oxygen concentration of gas travelling through output 110 towards a user.

Device 100 also includes user inputs 106 and 108. User inputs 106 and 108 allow a therapist, patient, etc. (collectively "a user") to enter, and device 100 to receive, adjustments to a one or more flow rates. For example, device 100 may receive inputs of gas from multiple gas sources. Device 100 may manage the flow rates of these gases to ensure that any gas flowing through output 110 towards a user has certain properties (e.g., a particular flow rate, oxygen concentration, temperature, etc.).

Figure 2:
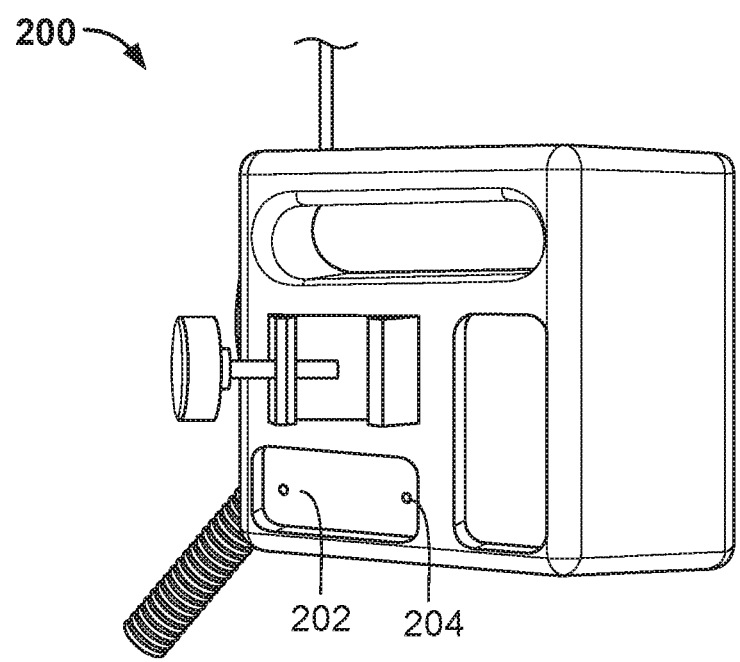
FIG. 2 shows another illustrative example of a device for obtaining desired oxygen concentrations and air flows in accordance with some embodiments of the disclosure.

FIG. 2 shows device 200, which in some embodiments, may correspond to device 100. Device 200 has inputs 202 and 204. Input 202 and 204 may be connected to sources of gas. For example, as opposed to devices that use high pressure gas, device 200 may receive gas from a gas source that is pressurize under fifty psi. In some embodiments, input 202 may correspond to an input from a source of breathable air and input 204 may correspond to an input of oxygen.

Device 200 may receive gases via inputs 202 and 204 and output the gases (e.g., via output 110 (FIG. 1)) after ensuring that the output gases have certain properties. For example, device 200 may increase or decrease the rate at which gas from inputs 202 and 204 are received in response to inputs received via user inputs 106 and 108 (FIG. 1)). For example, in response to receiving a user input (e.g., via user input 106 (FIG. 1)) to decrease the air flow rate, device 200 may decrease the amount of gas (e.g., breathable air) that is received via input 202. Likewise, in response to receiving a user input (e.g., via user input 108 (FIG. 1)) to decrease the oxygen flow rate, device 200 may decrease the amount of gas (e.g., oxygen) that is received via input 204.

It should be noted that device 200 may be designed to be a portable unit. For example, inputs 202 and 204 may be structured to receive various connections from various gas sources in order to provide universal connectivity to the different gas sources that may be encountered in various settings. Additionally or alternatively, device 200 may be accompanied by various components for use is facilitating the connection of various gas sources to inputs 202 and 204. Moreover, in some embodiments, device 200 may include batteries or power cords in order to remain powered wherever a user desired to administer therapy.

Figure 3:
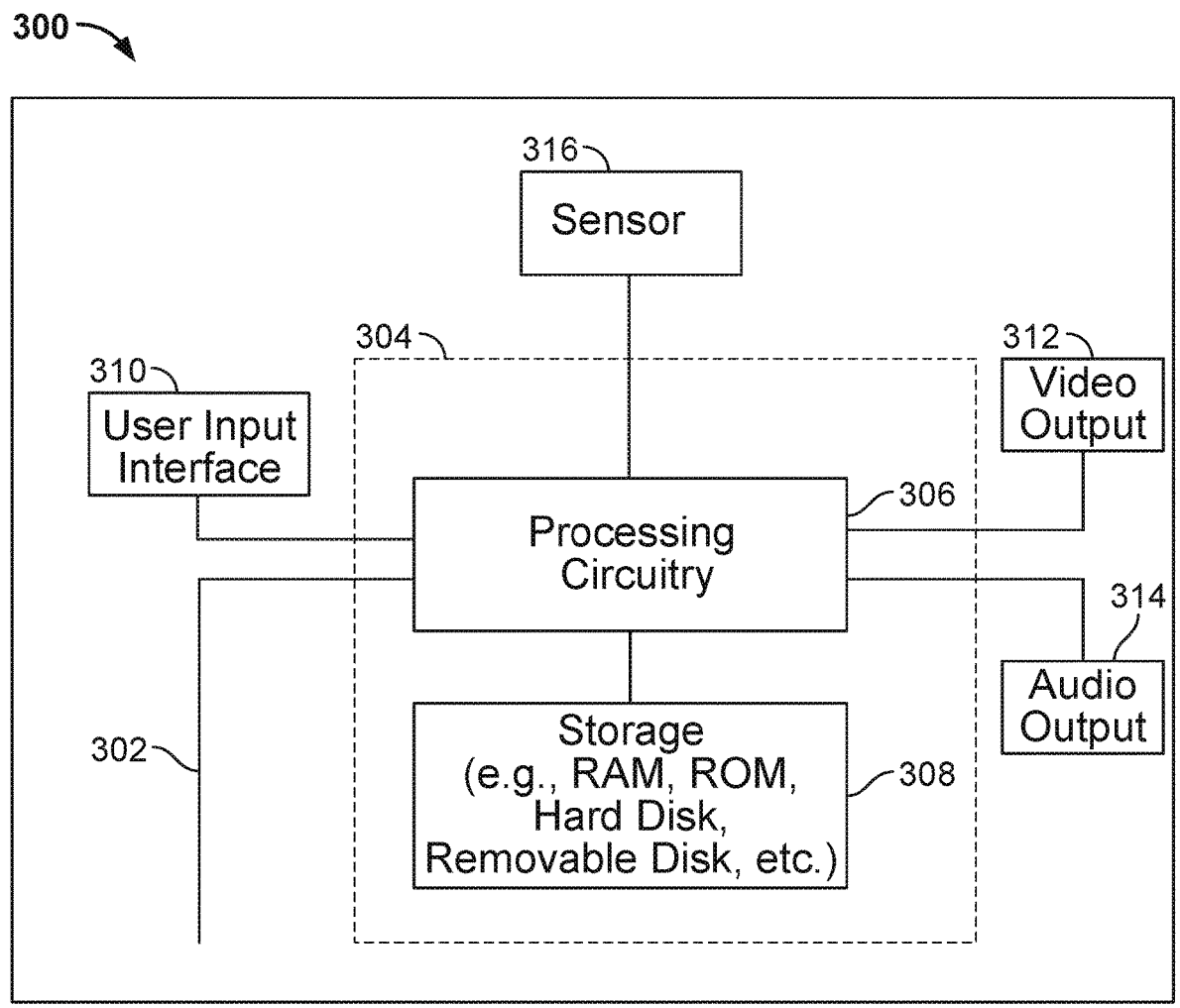
FIG. 3 is a block diagram of the circuitry in an illustrative device in accordance with some embodiments of the disclosure.

FIG. 3 is a block diagram of the circuitry in an illustrative device in accordance with some embodiments of the disclosure. For example, additionally or alternatively to the devices described in FIGS. 1-2, which provided built in inputs and outputs, the device may function as a set of instructions, encoded on computer readable media, for performing any of the embodiments discussed herein. Computer readable media includes any media capable of storing data. The computer readable media may be transitory, including, but not limited to, propagating electrical or electromagnetic signals, or may be non-transitory including, but not limited to, volatile and non-volatile computer memory or storage devices such as a hard disk, floppy disk, USB drive, DVD, CD, media cards, register memory, processor caches, Random Access Memory ("RAM"), etc.

For example, the device 300 may represent a stand-alone unit (e.g., as described in FIGS. 1-2) or may represent an application implemented on a device (e.g., a CPU) connected to various other components (e.g., a display screen or display device, a user input interface, gas inputs/outputs, etc.). The application may include the various instructions for performing the steps and functions described herein. Moreover, the application may transmit one or more instructions to a specific component (e.g., a display screen) to cause a function to be performed (e.g., a user interface to be generated for display).

As shown in FIG. 3, device 300 may receive/transmit instructions and data via input/output (hereinafter "I/O") path 302. I/O path 302 may provide content (e.g., an instruction related to a target oxygen concentration level) from a component incorporated into and/or accessible by the component upon which the application is implemented. For example, in some embodiments, instructions transmitted via I/O path 302 may be transmitted over a local area network (LAN) or wide area network (WAN).

The instructions for performing the steps and/or functions described herein may reside on an application implemented on control circuitry 304, which includes processing circuitry 306 and storage 308. Control circuitry 304 may be used to send and receive commands, requests, and other suitable data using I/O path 302. I/O path 302 may connect control circuitry 304 (and specifically processing circuitry 306) to one or more communications paths, sensors (e.g., sensor 316), etc. I/O functions may be provided by one or more of these communications paths.

Control circuitry 304 may be based on any suitable processing circuitry such as processing circuitry 306. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 304 executes instructions for an application stored in memory (i.e., storage 308). Specifically, control circuitry 304 may be instructed by the application to perform the functions discussed above and below. For example, the application may provide instructions to control circuitry 304 to generate for display indications on user interface 102 (FIG. 1)). In some implementations, any action performed by control circuitry 304 may be based on instructions received from the application implemented on control circuitry 304.

In client-server based embodiments, control circuitry 304 may include communications circuitry suitable for communicating with an application server or other networks or servers. The instructions for carrying out the above mentioned functionality may be stored on the application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths. In addition, communications circuitry may include circuitry that enables peer-to-peer communication of user equipment devices, or communication of user equipment devices in locations remote from each other (described in more detail below).

Memory may be an electronic storage device provided as storage 308 that is part of control circuitry 304. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, or any other suitable fixed or removable storage devices, and/or any combination of the same. Storage 308 may be used to store various types of instructions and data described herein. Nonvolatile memory may also be used (e.g., to launch a boot-up routine and other instructions). Cloud-based storage may be used to supplement storage 308 or instead of storage 308.

Control circuitry 304 may include video generating circuitry, such as one or more MPEG-2 decoders or other digital decoding circuitry or video circuits or combinations of such circuits. Encoding circuitry (e.g., for converting over-the-air, analog, or digital signals to MPEG signals for storage) may also be provided. Control circuitry 304 may also include scaler circuitry for upconverting and downconverting content into the preferred output format of device 300. Circuitry 304 may also include digital-to-analog converter circuitry and analog-to-digital converter circuitry for converting between digital and analog signals.

A user may send instructions to control circuitry 304 using user input interface 310. User input interface 310 may be any suitable user interface, such as a remote control, mouse, trackball, keypad, keyboard, touch screen, touchpad, stylus input, joystick, voice recognition interface, or other user input interfaces. User input interface 310 may constitute an input implemented at a device (e.g., user input 106 and 108 (FIG. 1)) or may be a stand-alone device (e.g., a remote control).

Display 312 may be provided as a stand-alone device or integrated with other elements of device 300. For example, display 312 may be a touchscreen or touch-sensitive display. In such circumstances, user input interface 310 may be integrated with or combined with display 312. Display 312 may be one or more of a monitor, a television, a liquid crystal display (LCD) for a mobile device, amorphous silicon display, low temperature poly silicon display, electronic ink display, electrophoretic display, active matrix display, electro-wetting display, electrofluidic display, cathode ray tube display, light-emitting diode display, electroluminescent display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. In some embodiments, display 312 may be HDTV-capable. In some embodiments, display 312 may be a 3D display, and the application and any suitable content may be displayed in 3D. A video card or graphics card may generate the output to the display 312. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 304. The video card may be integrated with the control circuitry 304.

Speakers 314 may be provided as integrated with other elements of user equipment device 300 or may be stand-alone units. The audio component of videos and other content displayed on display 312 may be played through speakers 314. In some embodiments, the audio may be distributed to a receiver (not shown), which processes and outputs the audio via speakers 314.

Control circuitry 304 may also transmit and/or receive instructions and data from sensor 316. It should be noted that in some embodiments control circuitry 304 may communicate with more than a single sensor; however, in order to not clutter the drawing only a single sensor is shown. In some embodiments, sensor 316 may determine a flow rate of gas from one or more sources. For example, sensor 316 may monitor the gas received via an input (e.g., inputs 202 and 204 (FIG. 2)). Moreover, in some embodiments, sensor 316 may include components (e.g., valves, etc.) for increasing or decreasing the flow rate received from an input. For example, in some embodiments, sensor 316 may function to open or close a value to enable to restrict gas flow to a desired level.

The application may be implemented using any suitable architecture. For example, it may be a stand-alone application wholly-implemented on device 300. In such an approach, instructions of the application are stored locally (e.g., in storage 308), and data for use by the application is downloaded on a periodic basis (e.g., from an out-of-band feed, from an Internet resource, or using another suitable approach). Control circuitry 304 may retrieve instructions of the application from storage 308 and process the instructions to generate any of the displays discussed herein. Based on the processed instructions, control circuitry 304 may determine what action to perform when input is received from input interface 310. For example, movement of a cursor on a display up/down may be indicated by the processed instructions when input interface 310 indicates that an up/down button was selected.

In some embodiments, the application is a client-server based application. Data for use by a thick or thin client implemented on device 300 is retrieved on-demand by issuing requests to a server remote to device 300. In one example of a client-server based application, control circuitry 304 runs a web browser that interprets web pages provided by a remote server. For example, the remote server may store the instructions for the application in a storage device. The remote server may process the stored instructions using circuitry (e.g., control circuitry 304) and generate the displays discussed above and below. The client device may receive the displays generated by the remote server and may display the content of the displays locally on device 300. This way, the processing of the instructions is performed remotely by the server while the resulting displays are provided locally on device 300.

Device 300 may receive inputs from the user via input interface 310 and transmit those inputs to the remote server for processing and generating the corresponding displays. For example, device 300 may transmit a communication to the remote server indicating that an up/down button was selected via input interface 310. The remote server may process instructions in accordance with that input and generate a display of the application corresponding to the input (e.g., a display that moves a cursor up/down). The generated display is then transmitted to equipment device 300 for presentation to the user.

In some embodiments, the application is downloaded and interpreted or otherwise run by an interpreter or virtual machine (run by control circuitry 304). In some embodiments, the application may be encoded in the ETV Binary Interchange Format (EBIF), received by control circuitry 304 as part of a suitable feed, and interpreted by a user agent running on control circuitry 304. For example, the application may be an EBIF application. In some embodiments, the application may be defined by a series of JAVA-based files that are received and run by a local virtual machine or other suitable middleware executed by control circuitry 304. In some of such embodiments (e.g., those employing MPEG-2 or other digital media encoding schemes), the application may be, for example, encoded and transmitted in an MPEG-2 object carousel with the MPEG audio and video packets of a program.

Figure 4:
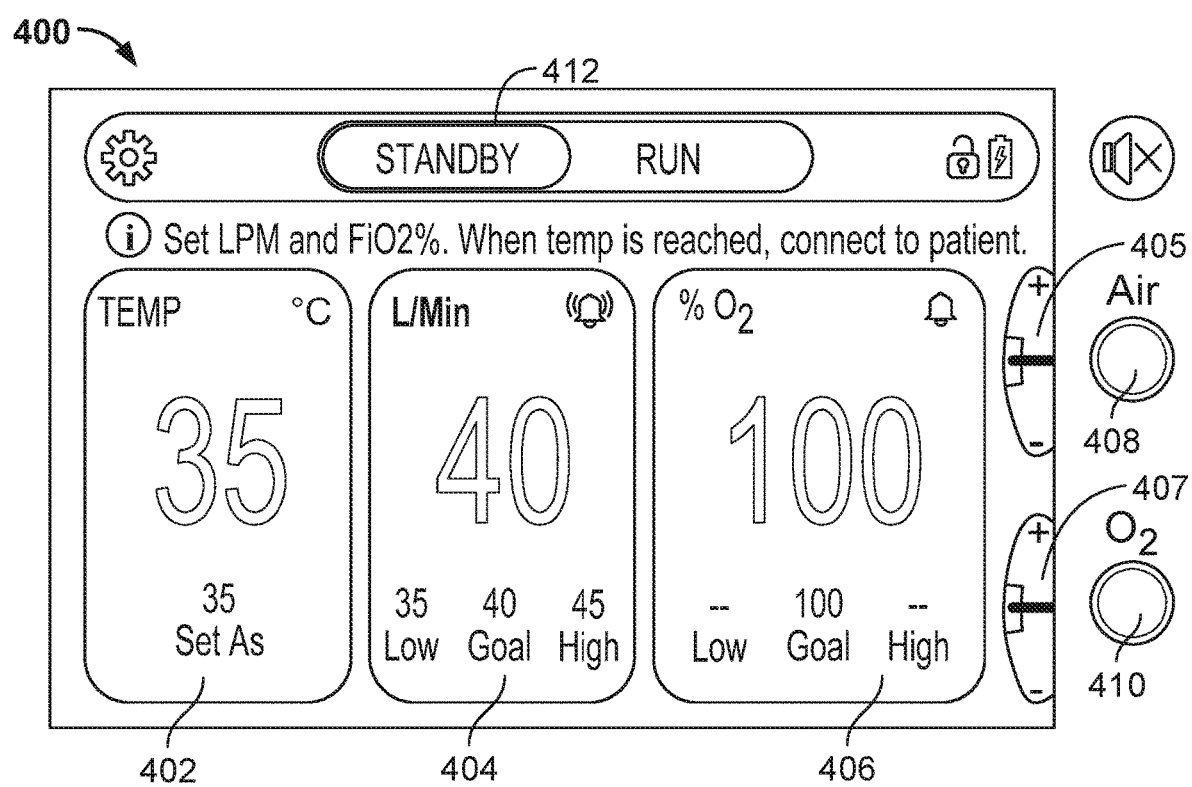
FIG. 4 shows an illustrative example of a user interface for a device for obtaining desired oxygen concentrations and air flows in accordance with some embodiments of the disclosure.

FIG. 4 shows an illustrative example of an interface for a device for obtaining desired oxygen concentrations and air flows in accordance with some embodiments of the disclosure. For example, FIG. 4 shows user interface 400 and includes examples of the indications that may be included in user interface 102 (FIG. 1).

User interface 400 includes information that may be included in one or more indications. For example, user interface 400 includes information cells 402, 404, and 406. Information cell 402 relates to a current temperature of gas received by a user. Information cell 404 relates to a current air flow rate of gas received by the user. Finally, information cell 406 relates to an oxygen concentration of gas received by the user.

User interface 400 also includes an indication of manual adjustments that may need to be made in order to achieve a targeted total flow rate and a targeted oxygen concentration. For example, user interface 400 includes gauge 405, which corresponds to the progress of the user towards a targeted total flow rate, and gauge 407, which corresponds to the progress of the user towards a targeted oxygen concentration. For example, as a user proceeds towards (or away) from a targeted total flow rate (e.g., via manually adjusting dial 408), gauge 405 may indicate that the user needs to increase or decrease the current air flow rate. Likewise, as a user proceeds towards (or away) from a targeted oxygen concentration (e.g., via manually adjusting dial 410), gauge 405 may indicate that the user needs to increase or decrease the current oxygen flow rate.

It should be noted, that as referred to herein an "indication" may include anything that communicates information to a user. For example, an indication may include any audio, video, and/or textual data that communicates information to a user. For example, an indication may include a reading on gauge 405 or other data (e.g., a temperature reading in information cell 402). In another example, an indication may include an audio alert (e.g., that a threshold oxygen concentration is not met). Moreover, an indication may communicates multiple types of information (e.g., a temperature reading in information cell 402 and an oxygen concentration reading is information cell 406) simultaneously. In some embodiments, a single indication may include all the information communicated to a user by a user interface (e.g., user interface 400) at one time. In such cases, different indications may correspond to the appearance of a user interface (e.g., user interface 400) at different points in time.

In some embodiments, indications may correspond to particular types of information. For example, an indication may refer to a temperature setting currently generated for display on a user interface (e.g., user interface 400). In another example, an indication may refer to a group of information types. For example, an indication may refer to the information that is related to the progress of a user towards a target (e.g., a targeted total flow rate and/or a targeted oxygen concentration). In such cases, an indication may correspond to the appearance of gauges 405 and 407 at a particular point in time.

It should also be noted that the appearance of gauges 405 and 407 are illustrative and not meant to be limiting. For example, while gauges 405 and 407 may appear in one form in FIG. 4, gauges 405 and 407 may appear in other forms in other embodiments. For example, video cues, audio tones, textual readouts, and/or any other way to communicate to a user about the progress towards a target and/or the need to manually adjust a flow rate would be an effective substitute for gauges 405 and 407. It should also be noted that the amount of information conveyed by gauges 405 and 407 may vary. For example, in some embodiments, gauges 405 and 407 may include information on whether or not a flow rate needs to be increased or decreased. Additionally or alternatively, gauges 405 and 407 may indicate how much (in an appropriate unit of measure) a flow rate needs to be increased or decreased.

In some embodiments, gauges 405 and 407 and/or appearance thereof may be customized based on a user. For example, a user may select a digital display as opposed to an analog display for gauge 405. Likewise, in some embodiments, gauge 405 and 407 may be calibrated for use with a particular user. For example, a user known to enjoy a higher level of precision when manually adjusting dial 408 may see a user interface with a more precise unit of measure (e.g., readings to two decimal points instead of none), than a user known to have no preference for a higher level of precision. Likewise, in response to determining that a user is having difficulties viewing a gauge in one form (e.g., analog readings), the device may present the gauge in a different form (e.g., digital readings).

Dials 408 and 410 also appear in FIG. 4. In some embodiments, dials 408 and 410 may correspond to user inputs 106 and 108 (FIG. 1). For example, dials 408 and 410 may provide a mechanism through which the device (e.g., device 100 (FIG. 1)) may receive user inputs manually adjusting the flow rate of gases. In some embodiments, dials 408 and 410 may appear as part of user interface 400. For example, dials 408 and 410 may appears on a touchscreen interface.

In FIG. 4, user interface 400 is currently in standby mode as indicated by icon 412. During standby mode, one or more function of the device may be turned off or inaccessible (e.g., in order to save power). Moreover, as shown by FIG. 4, user interface 400 may issue instructions for the operation of the device. For example, as shown in FIG. 4, user interface 400 currently prompts the user to "Set LPM and FiO2%. When temp is reached, connect to patient." As the device is moved to a non-standby mode (e.g., as described in FIG. 5), the device may provide other prompts to the user.

Figure 5:
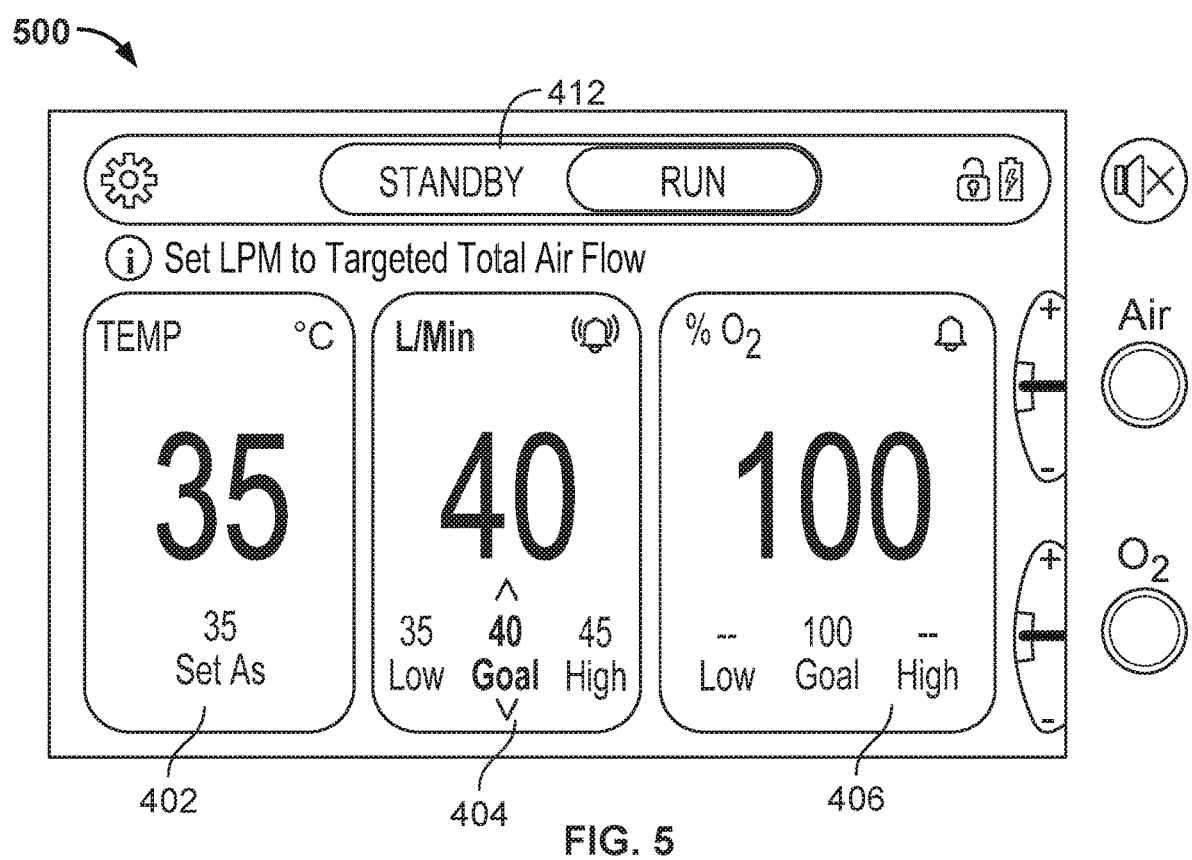
FIG. 5 shows another illustrative example of the user interface for a device for obtaining desired oxygen concentrations and air flows in accordance with some embodiments of the disclosure.

FIG. 5 shows another illustrative example of an interface for a device for obtaining desired oxygen concentrations and air flows in accordance with some embodiments of the disclosure. For example, FIG. 5 shows an example of the indications that may be included in user interface 102 (FIG. 1) after the device is powered on (or changed to a non-standby mode).

For example, as shown in FIG. 5, user interface 500 (which may correspond to user interface 400 (FIG. 4) when in a non standby mode) is currently in a "RUN" mode as indicated by icon 412. Moreover, the device prompts a user to enter a targeted total air flow rate (e.g., "Set LPM to targeted Total Air Flow"). For example, the device may receive one or more user inputs (e.g., via user input 104 (FIG. 1)) navigating between information cells 402, 404, and 406. Upon highlighting a particular information cell (e.g., information cell 404 as shown in FIG. 5), the device may receive subsequent user input selecting a desired targeted total air flow rate. Additionally, the device may prompt a user for minimum and maximum total air flows. For example, by establishing minimum and maximum air flows, the device may allow a user to establish a threshold total air flow. In FIG. 5, the total air flow minimum is set at thirty-five liters per minute, and the maximum total air flow is set at forty-five liters per minute. Accordingly, if the total air flow exceeds forty-five liters per minute or falls under thirty-five liters per minute, the device may alert the user.

Figure 6:
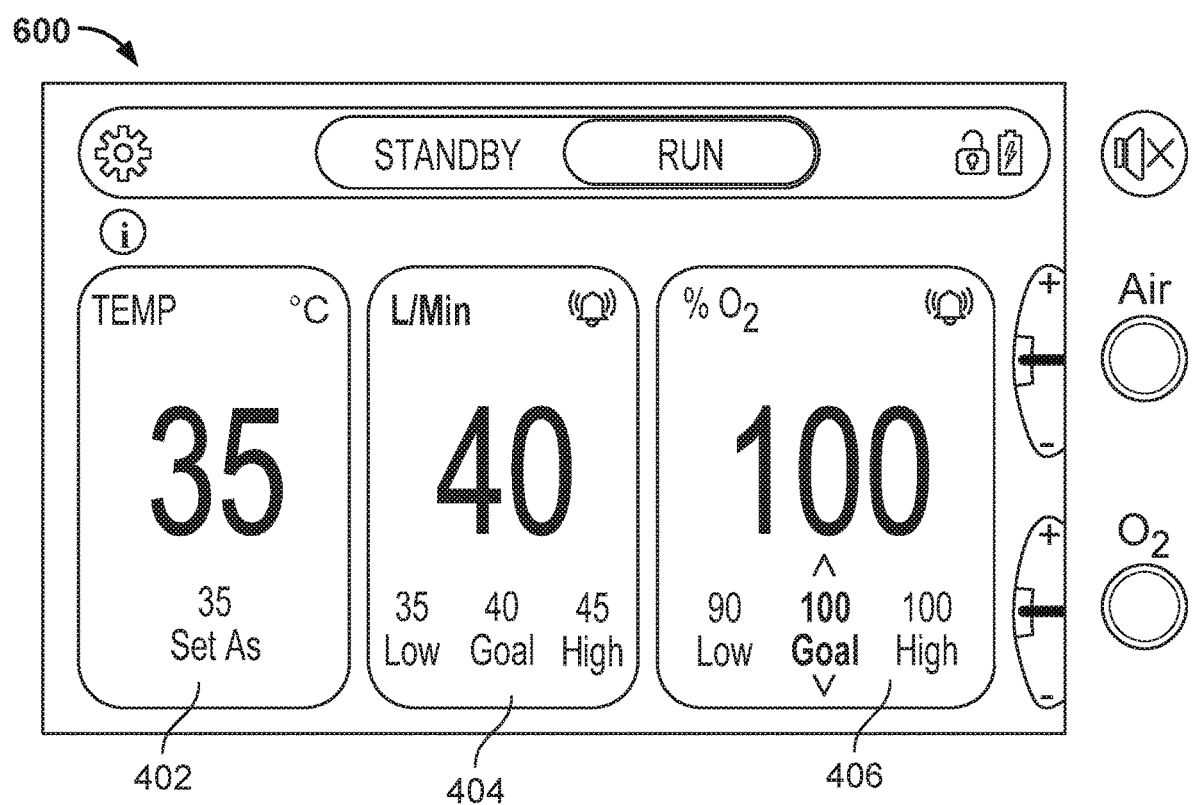
FIG. 6 shows another illustrative example of the user interface for a device for obtaining desired oxygen concentrations and air flows in accordance with some embodiments of the disclosure.

FIG. 6 shows another illustrative example of an interface for a device for obtaining desired oxygen concentrations and air flows in accordance with some embodiments of the disclosure. For example, FIG. 6 shows an example of the indications that may be included in user interface 102 (FIG. 1).

As shown in FIG. 6, user interface 600 has received one or more user inputs (e.g., via user input 104 (FIG. 1)) navigating to information cell 406. Upon highlighting information cell 406, the device may receive subsequent user inputs selecting a desired targeted oxygen concentration. Additionally, the device may prompt a user for minimum and maximum oxygen concentrations. For example, as described in relation to total air flow in FIG. 5, by establishing minimum and maximum oxygen concentrations, the device may allow a user to establish a threshold oxygen concentration. These thresholds may be used as the basis of whether or not an alert is triggered (e.g., as described in relation to FIG. 7). In the present case, the minimum oxygen concentration is set at ninety percent, and the targeted oxygen concentration and the maximum oxygen concentration are set at one-hundred percent.

Figure 7:
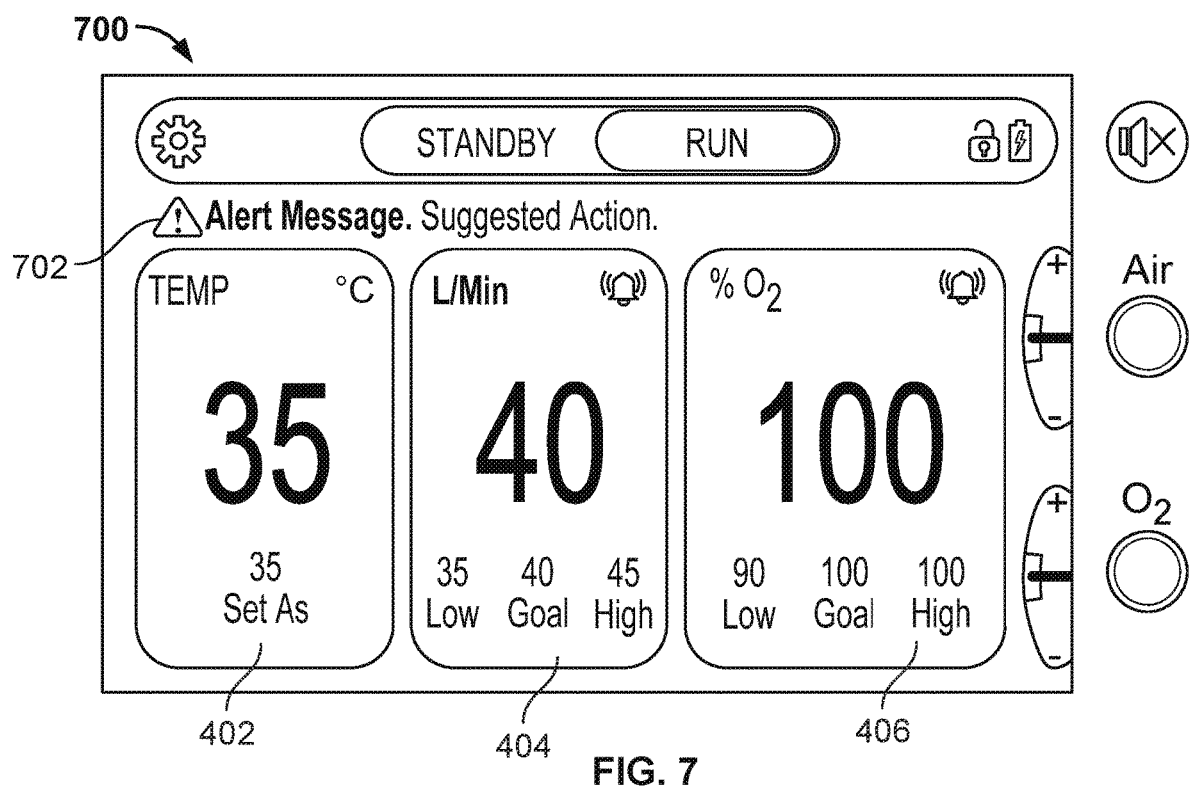
FIG. 7 shows another illustrative example of the user interface for a device for obtaining desired oxygen concentrations and air flows in accordance with some embodiments of the disclosure.

FIG. 7 shows another illustrative example of an interface for a device for obtaining desired oxygen concentrations and air flows in accordance with some embodiments of the disclosure. For example, FIG. 7 shows an example of the indications that may be included in user interface 102 (FIG. 1).

As shown in FIG. 7, the device has received a user input of a targeted total air flow and targeted oxygen concentration. Moreover, as shown by user interface 700, as the targeted oxygen concentration (e.g., currently reading at one-hundred percent) corresponds to the maximum oxygen concentration (e.g., also one-hundred percent). Accordingly, a threshold may have been met, triggering alert 702.

For example, in some embodiments, the device may retrieve a threshold oxygen concentration (e.g., corresponding to the maximum oxygen concentration appearing in information cell 406). The device may then determine an oxygen concentration (e.g., based on a comparison of the differences between a current air flow rate, current oxygen flow rate, and their respective target rates that would produce a particular oxygen concentration) and compare the threshold oxygen concentration to the determined oxygen concentration. In response to determining that the current oxygen concentration is less than, equal to, or more than the threshold oxygen concentration (e.g., depending on the threshold being met), the device generating for display, as shown in user interface 700, an alert.

In another example, the device may retrieve a threshold oxygen flow rate. The device may then compare the threshold oxygen flow rate to a current oxygen flow rate. In response to determining that the first oxygen flow rate is less than, equal to, or more than the threshold oxygen flow rate (e.g., depending on the threshold being met), the device generating for display, as shown in user interface 700, an alert.

Figure 8:
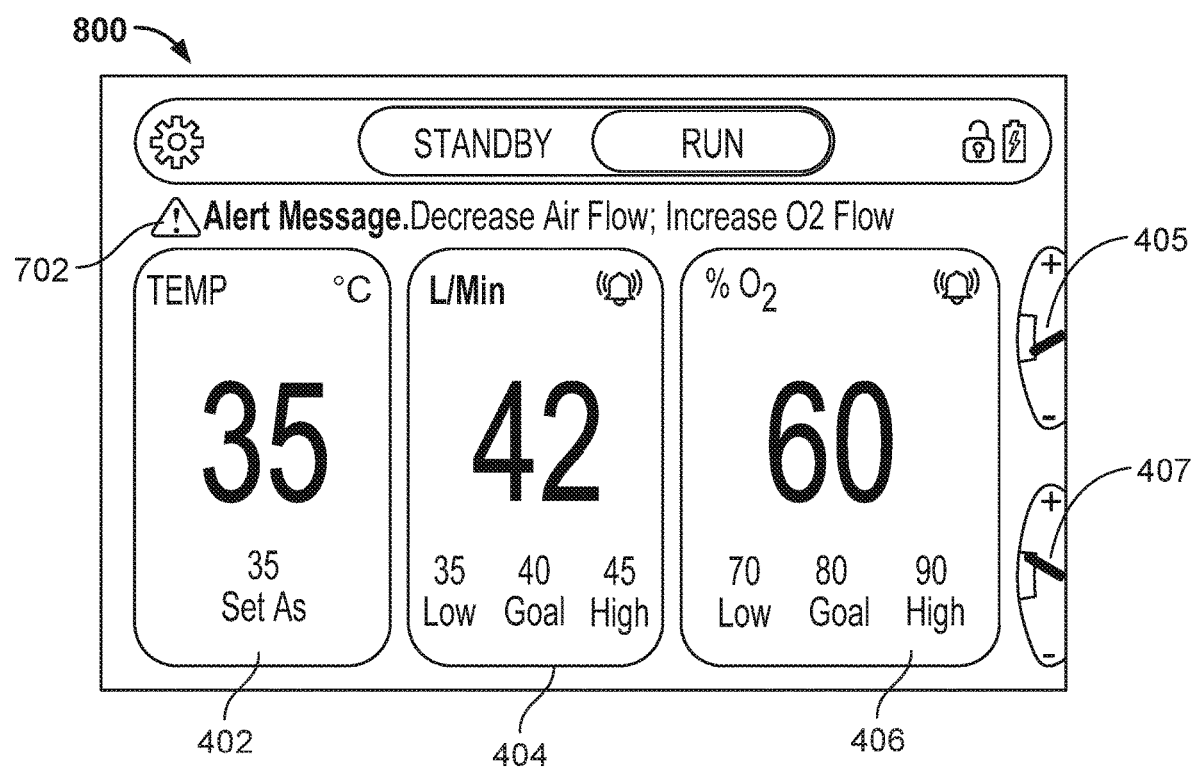
FIG. 8 shows another illustrative example of the user interface for a device for obtaining desired oxygen concentrations and air flows in accordance with some embodiments of the disclosure.

FIG. 8 shows another illustrative example of an interface for a device for obtaining desired oxygen concentrations and air flows in accordance with some embodiments of the disclosure. For example, FIG. 8 shows an example of the indications that may be included in user interface 102 (FIG. 1) while the device in operation.

As shown in FIG. 8, as indicated by user interface 800, the targeted total air flow rate is forty liters per minute and the targeted oxygen concentration is eighty percent. Furthermore, the device has determined that the current total air flow is forty-two liters per minute and the current oxygen concentration is at sixty percent. In response, the device has determined that changes to the air flow rate and the oxygen flow rate are necessary to achieve the targeted total air flow rate and the targeted oxygen concentration.

In response to the determination, the device has generated for display an indication on user interface 800 that indicates an amount to manually adjust the air flow rate and the oxygen flow rate. For example, as shown in FIG. 8, gauge 405 and 407 now indicate that the air flow rate and the oxygen flow rate should be manually adjusted. Specifically, user interface 800 includes an indication that the air flow rate should be decreased and that the oxygen flow rate should be increased. Additionally, alert 702 now prompts the user to "Decrease Air Flow; Increase o2 Flow."

FIG. 9 shows an illustrative example of pseudocode for obtaining desired oxygen concentrations and air flows. For example, through the use of process 900, device 100 (FIG. 1)) may determine whether or not an indication to manually adjust an air flow rate or an oxygen flow rate should be generated for display (e.g., on user interface 106 (FIG. 1)). It should be noted that process 900 is illustrative only and should not be taken to be limiting.

At lines 1-4, process 900 issues various incorporation function calls via an include directive. The incorporation function calls incorporate other functions used to perform other tasks such as generating a user interface (e.g., user interface 106 (FIG. 1)) or initializing an oxygen and/or air flow sensor (e.g., sensor 316 (FIG. 3)).

At lines 5-19, process 900 begins a subroutine to determine whether or not indicate to a user that a manual adjustment to an air flow rate or oxygen flow rate (e.g., via input 106 and 108 (FIG. 1)) is necessary. During lines 5-19, various variable values are establish. For example, the targeted oxygen concentration and targeted total flow may be received via a user input (e.g., as described in relation to FIGS. 4-8). For example, the device may receive one or more user inputs (e.g., via user input interface 310 (FIG. 3)) establishing a target oxygen concentration of twenty-one percent and a targeted total air flow of ten liters per minute.

At lines 19-25, process 900 begins a subroutine to establish a target oxygen concentration. Process 900 normalizes the target oxygen concentration value entered by a user such that a target oxygen concentration below twenty-one percent (e.g., the amount of oxygen concentration in breathable air) is set for twenty-one percent, and a target oxygen concentration above one-hundred percent is set at one-hundred percent.

At lines 26-32, process 900 begins a subroutine to establish a target total air flow. Process 900 normalizes the target total air flow value entered by a user such that a target total air flow below one liter per minute is set at one liter per minute, and a target total air flow above forty liters per minute is set at forty liters per minute.

At lines 33-43, process 900 begins a subroutine to determine whether or not a manual adjustment of an air flow rate or oxygen flow rate should be indicated to a user.

At line 35, process 900 determines a target air flow by multiplying a target total air flow (e.g., received via user input interface 310 (FIG. 3)) and the result of one minus the target oxygen concentration (e.g., received via user input interface 310 (FIG. 3)) divided by one-hundred (e.g., in order to obtain a percent) and further divided by the percentage of breathable air (e.g., found in the air from the air source) that is not oxygen (e.g., seventy-nine). For example, at line 35, process 900 determines a target air flow by multiplying the target total air flow and the ratio of an oxygen percentage of the targeted oxygen concentration to an oxygen percentage in the air from the air source.

At line 36, process 900 determines a target oxygen flow by subtracting the target air flow determined in line 35 from the target total air flow (e.g., received via user input interface 310 (FIG. 3)).

At lines 37-38, process 900 determines the actual total air flow (e.g., received via inputs 202 and 204 (FIG. 2)). At line 39, process 900 determines the actual air flow by multiplying the actual total air flow determined in line 37 and the result of one minus the oxygen concentration determined in line 38 (e.g., twenty-one) divided by one-hundred (e.g., in order to obtain a percent) and further divided by the percentage of breathable air (e.g., found in the air from the air source) that is not oxygen (e.g., seventy-nine). For example, at line 39, process 900 determines actual air flow by multiplying the actual total air flow determined in line 37 and the ratio of an oxygen percentage of the actual oxygen flow to an oxygen percentage in the air from the air source.

At line 41, process 900 determines a difference between the actual air flow rate (e.g., the air received via input 202 (FIG. 2)) and the targeted air flow rate (e.g., determined to achieve the targeted total air flow and targeted oxygen concentration requested by the user). At line 42, process 900 determines a difference between the actual oxygen flow rate (e.g., the oxygen received via input 204 (FIG. 2)) and the targeted oxygen flow rate (e.g., determined to achieve the targeted total air flow and targeted oxygen concentration requested by the user).

Figure 10:
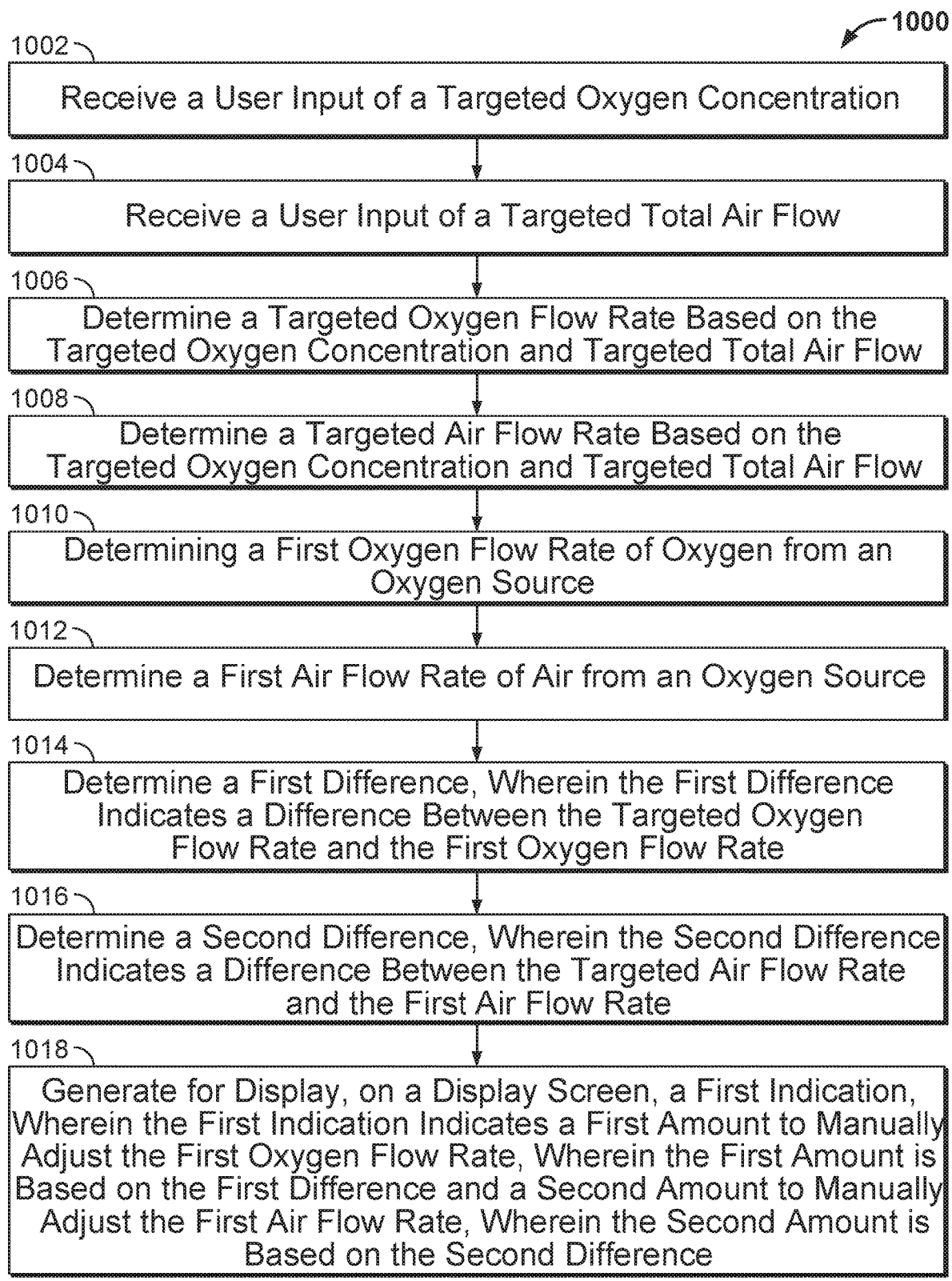
FIG. 10 shows an exemplary process for obtaining desired oxygen concentrations and air flows in accordance with some embodiments of the disclosure.

FIG. 10 shows an exemplary process for obtaining desired oxygen concentrations and air flows. Process 1000 may be used to update an indication (e.g., a reading on gauge 405 (FIG. 4)) on a user interface (e.g., user interface 106 (FIG. 1)). It should be noted that process 1100 or any step thereof, could occur on, or be provided by, any of the devices shown in FIGS. 1-3.

At step 1002, the device (e.g., control circuitry 304 (FIG. 3)) receives a user input (e.g., via user input interface 310 (FIG. 3)) of a targeted oxygen concentration. For example, the device may receive a user input (e.g., via user input 104 (FIG. 4)) selecting a targeted oxygen concentration. At step 1004, the device (e.g., control circuitry 304 (FIG. 3)) receives a user input (e.g., via user input interface 310 (FIG. 3)) of a targeted total air flow. For example, the device may receive a user input (e.g., via user input 104 (FIG. 4)) selecting a targeted total air flow. For example, the device allows a therapist or patient to input a specific oxygen concentration and a specific total air flow (e.g., tailored to levels to allow the patient to comfortably eat, speak, and sleep, while receiving the respiratory therapy).

At step 1006, the device (e.g., control circuitry 304 (FIG. 3)) determines a targeted oxygen flow rate based on the targeted oxygen concentration and the targeted total air flow. For example, using a ratio of an oxygen percentage of the targeted oxygen concentration to an oxygen percentage in the air from the air source, the device (e.g., control circuitry 304 (FIG. 3)) automatically selects the targeted air flow rate based on the ratio.

At step 1008, the device (e.g., control circuitry 304 (FIG. 3)) determines a targeted air flow rate based on the targeted oxygen flow rate and targeted total air flow. For example, to meet the targeted oxygen flow rate and targeted total air flow, the device (e.g., control circuitry 304 (FIG. 3)) must select a specific flow rate of the both air source and the oxygen source. As the device (e.g., control circuitry 304 (FIG. 3)) previously determined the targeted oxygen flow rate, the device (e.g., control circuitry 304 (FIG. 3)) subtracts the targeted oxygen flow rate from the targeted total flow rate to determine the targeted air flow rate.

At step 1010, the device (e.g., control circuitry 304 (FIG. 3)) determines a first oxygen flow rate of oxygen from an oxygen source. For example, the device (e.g., control circuitry 304 (FIG. 3)) may determine (e.g., via sensor 316 (FIG. 3)) the rate at which oxygen is flowing into the device via input 204 (FIG. 2)). At step 1012, the device (e.g., control circuitry 304 (FIG. 3)) determines a first air flow rate of air from an air source. For example, the device (e.g., control circuitry 304 (FIG. 3)) may determine (e.g., via sensor 316 (FIG. 3)) the rate at which air is flowing into the device via input 202 (FIG. 2)). For example, to determine the progress of the patient towards the targeted air flow rate and the targeted oxygen flow rate, the device determines an initial oxygen flow rate and air flow rate.

At step 1014, the device (e.g., control circuitry 304 (FIG. 3)) determines a first difference, wherein the first difference indicates a difference between the targeted oxygen flow rate and the first oxygen flow rate. At step 1016, the device (e.g., control circuitry 304 (FIG. 3)) determines a second difference, wherein the second difference indicates a difference between the targeted air flow rate and the first air flow rate. For example, the device (e.g., control circuitry 304 (FIG. 3)) may determine the differences between the targeted oxygen flow rate and initial oxygen flow rate and the targeted air flow rate and the initial air flow rate.

At step 1018, the device (e.g., control circuitry 304 (FIG. 3)) generates for display, on a display screen, a first indication, wherein the first indication indicates a first amount to manually adjust the first oxygen flow rate, wherein the first amount is based on the first difference and a second amount to manually adjust the first air flow rate, wherein the second amount is based on the second difference. For example, in response to determining that the oxygen flow rate must be increased or decreased to reach the targeted oxygen flow rate (associated with both the targeted oxygen concentration and the targeted total air flow) and that the air flow rate must be increased or decreased to reach the targeted oxygen flow rate (associated with both the targeted oxygen concentration and the targeted total air flow), the device (e.g., control circuitry 304 (FIG. 3)) may recommend adjustments to the current air flow rate and oxygen flow rate. The recommendations may appear as indications (e.g., gauges 405 and 407 (FIG. 4)) on a user interface (e.g., user interface 106 (FIG. 1)).

In some embodiments, the device (e.g., control circuitry 304 (FIG. 3)) may receive a first manual adjustment, in which the first manual adjustment modifies the first oxygen flow rate to a second oxygen flow rate. Accordingly, the device (e.g., control circuitry 304 (FIG. 3)) may determine a third difference that indicates a difference between the targeted oxygen flow rate and the second oxygen flow rate and generate for display, on the display screen, a second indication that indicates a second amount to manually adjust the second oxygen flow rate based on the third difference. For example, as the therapist or patient manually adjusts the oxygen flow rate in response to the first indication, the device (e.g., control circuitry 304 (FIG. 3)) may continuously update the degree to which further adjustment is needed. By providing this real-time feedback, the therapist or patient may quickly and easily reach the desired oxygen flow rate.

Furthermore, the device (e.g., control circuitry 304 (FIG. 3)) may receive a second manual adjustment that modifies the first air flow rate to a second air flow rate. Accordingly, the device (e.g., control circuitry 304 (FIG. 3)) may determine a fourth difference that indicates a difference between the targeted air flow rate and the second total air flow rate and the second indication may further indicate a second amount to manually adjust the second air flow rate based on the fourth difference. For example, the oxygen and air flow rates must be done in concert in order to achieve the desired total air flow and oxygen concentration, the device may continuously update the indications of the manual adjustments to each flow rate as needed. Consequently, a therapist or patient may modify both flow rates simultaneously or, simply adjust one flow rate and then the other.

In some embodiments, the device (e.g., control circuitry 304 (FIG. 3)) may provide additional feedback to the user. For example, the device may indicate the temperature, humidity, etc. of the gases delivered to the patient (e.g., in order to maximize comfort) as shown in FIGS. 4-7. Likewise, the device (e.g., control circuitry 304 (FIG. 3)) may allow the therapist or patient to set up various alerts (e.g., as discussed above). For example, the device may be configured sound and/or display an alert is a particular flow rate, concentration, etc. is below a safety or comfort threshold.

Figure 11:
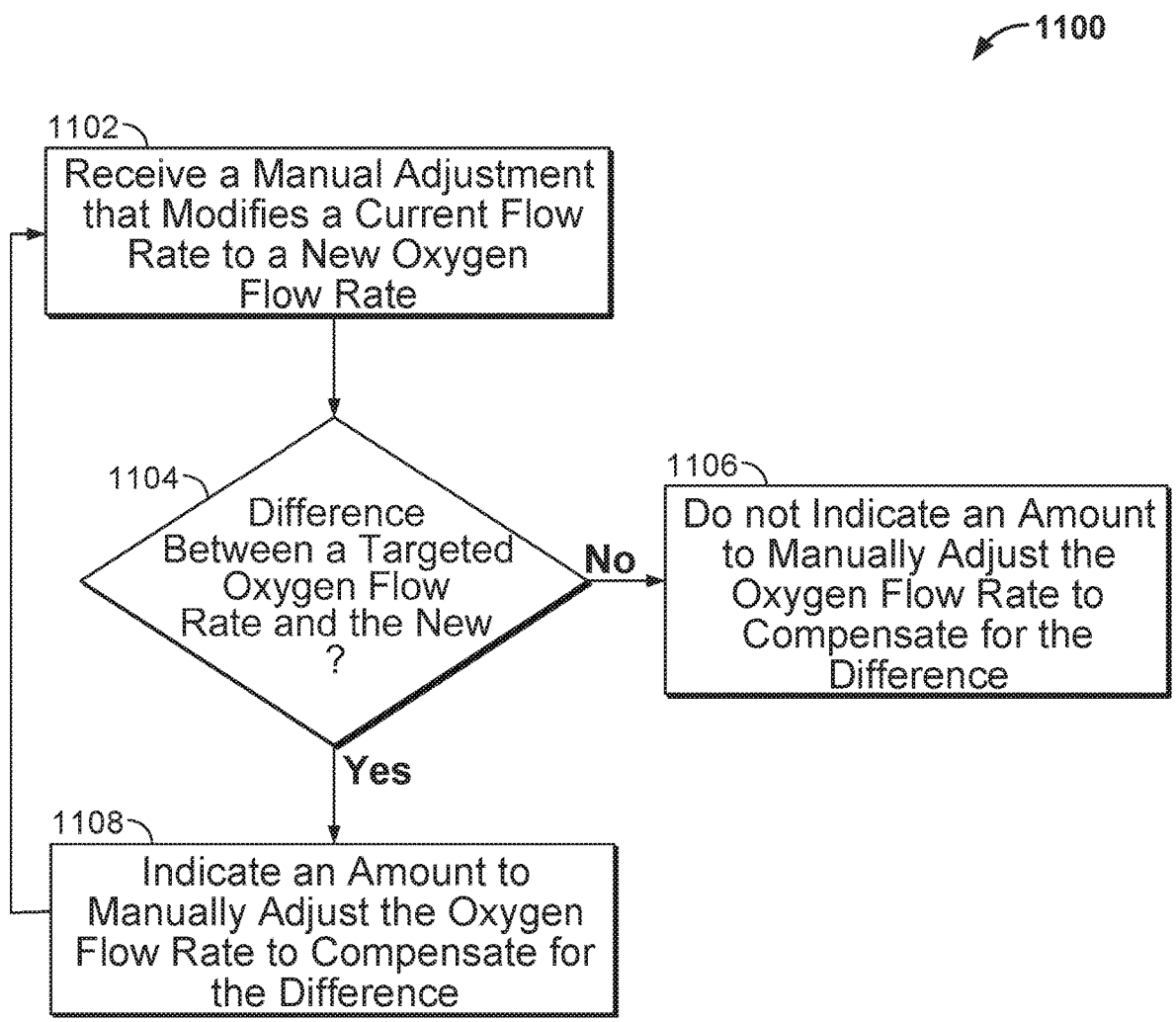
FIG. 11 shows an exemplary process for updating an indication in accordance with some embodiments of the disclosure.

FIG. 11 shows an exemplary process for updating an indication. Process 1100 may be used to update an indication (e.g., a reading on gauge 405 (FIG. 4)) on a user interface (e.g., user interface 106 (FIG. 1)). It should be noted that process 1100 or any step thereof, could occur on, or be provided by, any of the devices shown in FIGS. 1-3.

At step 1102, the device (e.g., control circuitry 304 (FIG. 3)) receives a manual adjustment that modifies a current oxygen flow rate to a new oxygen flow rate. For example, in response to determining that a targeted oxygen concentration or a targeted total air flow has not yet been achieved, the device (e.g., control circuitry 304 (FIG. 3)) may generate for display an indication (e.g., gauges 405 and 407 (FIG. 4)) indicating an amount to which a user should manually adjust a first air flow and/or a first oxygen flow rate. After receiving the adjustment (e.g., via user input interface 310 (FIG. 3)), the device (e.g., control circuitry 304 (FIG. 3)) may determine whether the target oxygen concentration has been reached.

At step 1104, the device (e.g., control circuitry 304 (FIG. 3)) determines a difference between a targeted oxygen flow rate and the new oxygen flow rate. For example, as directly testing the oxygen concentration delivered to the user would require additional, expensive equipment, the device (e.g., control circuitry 304 (FIG. 3)), determines a difference between the targeted oxygen flow rate (e.g., determined to correspond to the targeted oxygen concentration) and the current oxygen flow rate.

If the device (e.g., control circuitry 304 (FIG. 3)) determines that there is no difference between the current oxygen flow rate and the targeted oxygen flow rate, the device (e.g., control circuitry 304 (FIG. 3)) proceeds to step 1106 and does not indicate an amount to manually adjust the oxygen flow rate to compensate for the difference. For example, a user interface (e.g., user interface 106 (FIG. 1)) may not include an indication of an amount that the current oxygen flow rate needs to be modified in order to obtain the targeted oxygen concentration. In contrast, if the device (e.g., control circuitry 304 (FIG. 3)) determines that there is a difference between the current oxygen flow rate and the targeted oxygen flow rate, the device (e.g., control circuitry 304 (FIG. 3)) proceeds to step 1108 and indicates an amount to manually adjust the oxygen flow rate to compensate for the difference. For example, a user interface (e.g., user interface 106 (FIG. 1)) may include an indication of an amount that the current oxygen flow rate needs to be modified in order to obtain the targeted oxygen concentration.

It should be noted that in some embodiments, process 1100 may be continued and a difference between a targeted air flow rate and a current air flow rate may be determined. For example, after the device (e.g., control circuitry 304 (FIG. 3)) determines that the oxygen flow rate corresponds to the targeted oxygen flow rates required for achieving the targeted oxygen concentration, the device (e.g., control circuitry 304 (FIG. 3)) may continue to indicate whether or not a manually adjustment to the current air flow rate is necessary to achieve the targeted oxygen concentration and/or the total air flow.

It is contemplated that the steps or descriptions of FIGS. 10-11 may be used with any other embodiment of this disclosure. In addition, the steps and descriptions described in relation to FIGS. 7-11 may be done in alternative orders or in parallel to further the purposes of this disclosure. For example, each of these steps may be performed in any order or in parallel or substantially simultaneously to reduce lag or increase the speed of the system or method.

The processes discussed above are intended to be illustrative and not limiting. One skilled in the art would appreciate that the steps of the processes discussed herein may be omitted, modified, combined, and/or rearranged, and any additional steps may be performed without departing from the scope of the invention. More generally, the above disclosure is meant to be exemplary and not limiting. Only the claims that follow are meant to set bounds as to what the present invention includes. Furthermore, it should be noted that the features and limitations described in any one embodiment may be applied to any other embodiment herein, and flowcharts or examples relating to one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted, the systems and/or methods described above may be applied to, or used in accordance with, other systems and/or methods.

What is claimed is:

1. A method for guiding user adjustment of respiratory therapy, the method comprising:
   receiving, as a user input, a targeted oxygen concentration and a targeted total air flow;
   determining a first oxygen difference, wherein the first oxygen difference indicates a difference between a targeted oxygen flow rate and a first oxygen flow rate measured at a sensor of an oxygen valve, wherein the targeted oxygen flow rate is based on the targeted oxygen concentration and targeted total air flow;
   determining a first air difference, wherein the first air difference indicates a difference between a targeted air flow rate and a first air flow rate measured at a sensor of an air valve, wherein the targeted air flow rate is based on the targeted oxygen flow rate and the targeted total air flow;
   generating for display, on a display screen, a first adjustment instruction, wherein the first adjustment instruction indicates:
      a first oxygen amount to manually adjust the oxygen valve to control the first oxygen flow rate to reach the targeted oxygen concentration, wherein the first oxygen amount is based on the first oxygen difference; and
      a first air amount to manually adjust the air valve to control the first air flow rate to reach the targeted total air flow, wherein the first air amount is based on the first air difference; and
   generating for display on the display screen, in response to receiving a first manual adjustment of the valve to control the first oxygen flow rate or to control the first air flow rate, a second adjustment instruction that includes a notice to additionally increase or decrease the first oxygen flow rate or the first air flow rate to reach the targeted oxygen concentration or the targeted total air flow;
   wherein the notice includes a direction for adjustment of a knob controlling the oxygen valve or the air valve, the direction being opposite a direction of the first manual adjustment of the air valve or the oxygen valve, respectively.

2. The method of claim 1, further comprising receiving a second manual adjustment, wherein the second manual adjustment modifies the first oxygen flow rate to a second oxygen flow rate.

3. The method of claim 2, further comprising determining a second oxygen difference, wherein the second oxygen difference indicates a difference between the targeted oxygen flow rate and the second oxygen flow rate.

4. The method of claim 3, further comprising generating for display, on the display screen, a third adjustment instruction, wherein the third adjustment instruction indicates a second oxygen amount to manually adjust the second oxygen flow rate, wherein the second oxygen amount is based on the second oxygen difference.

5. The method of claim 4, further comprising receiving a third manual adjustment, wherein the third manual adjustment modifies the first air flow rate to a second air flow rate.

6. The method of claim 5, further comprising determining a second air difference, wherein the second air difference indicates a difference between the targeted air flow rate and the second total air flow rate.

7. The method of claim 6, wherein the third adjustment instruction further indicates a second air amount to manually adjust the second air flow rate, wherein the second air amount is based on the second air difference.

8. The method of claim 1, wherein the targeted air flow rate is determined based on the targeted oxygen concentration and targeted total air flow by:
determining a ratio of an oxygen percentage of the targeted oxygen concentration to an oxygen percentage in the air from an air source; and
selecting the targeted air flow rate based on the ratio.

9. The method of claim 1, further comprising:
retrieving a threshold oxygen flow rate; comparing the threshold oxygen flow rate to the first oxygen flow rate; and
in response to determining that the first oxygen flow rate is less than the threshold oxygen flow rate, generating for display, on the display screen, an alert.

10. The method of claim 1, wherein the first adjustment instruction further indicates a temperature of the air.

11. The method of claim 1, wherein the knob is next to an indicator on which the notice is indicated.

12. The method of claim 1, further comprising:
continuously updating the second adjustment instruction until the target oxygen flow rate is reached.

13. A system for guiding user adjustment of respiratory therapy, the system comprising:
input circuitry configured to:
receive, as a user input, a targeted oxygen concentration and a targeted total air flow;
control circuitry configured to:
determine a first oxygen difference, wherein the first oxygen difference indicates a difference between a targeted oxygen flow rate and a first oxygen flow rate measured at an oxygen sensor of an oxygen valve, wherein the targeted oxygen flow rate is based on the targeted oxygen concentration and targeted total air flow;
determine a first air difference, wherein the first air difference indicates a difference between a targeted air flow rate and a first air flow rate measured at an air sensor of an air valve, wherein the targeted air flow rate is based on the targeted oxygen flow rate and the targeted total air flow;
generate for display, on a display screen, a first adjustment instruction, wherein the first adjustment instruction indicates:
a first oxygen amount to manually adjust the oxygen valve to control the first oxygen flow rate to reach the targeted oxygen concentration, wherein the first oxygen amount is based on the first oxygen difference; and
a first air amount to manually adjust the air valve to control the first air flow rate to reach the targeted total air flow, wherein the first air amount is based on the first air difference; and
generate for display on the display screen, in response to receiving a first manual adjustment of the oxygen valve or the air valve, a second adjustment instruction that includes a notice to additionally increase or decrease the first oxygen flow rate or the first air flow rate to reach the targeted oxygen concentration or the targeted total air flow,
wherein the notice includes a direction for adjustment of a knob controlling the oxygen valve or the air valve, the direction being opposite a direction of the first manual adjustment of the air valve or the oxygen valve, respectively.

14. The system of claim 13, wherein the input circuitry is further configured to receive a second manual adjustment, wherein the second manual adjustment modifies the first oxygen flow rate to a second oxygen flow rate.

15. The system of claim 14, wherein the control circuitry is further configured to determine a second oxygen difference, wherein the second oxygen difference indicates a difference between the targeted oxygen flow rate and the second oxygen flow rate.

16. The system of claim 15, wherein the control circuitry is further configured to generate for display, on the display screen, a third adjustment instruction, wherein the third adjustment instruction indicates a second oxygen amount to manually adjust the second oxygen flow rate, wherein the second oxygen amount is based on the second oxygen difference.

17. The system of claim 16, wherein the input circuitry is further configured to receive a third manual adjustment, wherein the third manual adjustment modifies the first air flow rate to a second air flow rate.

18. The system of claim 17, wherein the control circuitry is further configured to determine a second air difference, wherein the second air difference indicates a difference between the targeted air flow rate and the second total air flow rate.

19. The system of claim 18, wherein the third adjustment instruction further indicates a second air amount to manually adjust the second air flow rate, wherein the second air amount is based on the second air difference.

20. The system of claim 13, wherein the control circuitry is configured to determine the targeted air flow rate based on the targeted oxygen concentration and targeted total air flow by:
determining a ratio of an oxygen percentage of the targeted oxygen concentration to an oxygen percentage in the air from an air source; and
selecting the targeted air flow rate based on the ratio.

21. The system of claim 13, wherein the control circuitry configured to:
retrieve a threshold oxygen flow rate;
compare the threshold oxygen flow rate to the first oxygen flow rate; and in response to determining that the first oxygen flow rate is less than the threshold oxygen flow rate, generate for display, on the display screen, an alert.

22. The system of claim 13, wherein the first adjustment instruction further indicates a temperature of the air.

23. A non-transitory computer readable medium having instructions recorded thereon for guiding user adjustment of respiratory therapy, the instructions comprising:
- an instruction for determining a first oxygen difference, wherein the first oxygen difference indicates a difference between a targeted oxygen flow rate and a first oxygen flow rate measured at an oxygen sensor of an oxygen valve, wherein the targeted oxygen flow rate is based on a targeted oxygen concentration and a targeted total air flow;
- an instruction for determining a first air difference, wherein the first air difference indicates a difference between a targeted air flow rate and a first air flow rate measured at an air sensor of an air valve, wherein the targeted air flow rate is based on the targeted oxygen flow rate and the targeted total air flow;
- an instruction for generating for display, on a display screen, a first adjustment instruction, wherein the first adjustment instruction indicates:
  - a first oxygen amount to manually adjust the oxygen valve to control the first oxygen flow rate to reach the targeted oxygen concentration, wherein the first oxygen amount is based on the first oxygen difference; and
  - a first air amount to manually adjust the air valve to control the first air flow rate to reach the targeted total air flow, wherein the first air amount is based on the first air difference; and
- an instruction for generating for display on the display screen, in response to receiving a first manual adjustment of the oxygen valve or the air valve, a second adjustment instruction that includes a notice to additionally increase or decrease the first oxygen flow rate or the first air flow rate to reach the targeted oxygen concentration or the targeted total air flow,
- wherein the notice includes a direction for adjustment of a knob controlling the oxygen valve or the air valve, the direction being opposite a direction of the first manual adjustment of the air valve or the oxygen valve, respectively.

* * * * *